United States Patent
Zhang et al.

(10) Patent No.: US 10,738,112 B2
(45) Date of Patent: Aug. 11, 2020

(54) ANTI-HUMAN INTERLEUKIN-17A MONOCLONAL ANTIBODY

(71) Applicant: SUNSHINE GUOJIAN PHARMACEUTICAL (SHANGHAI) CO., LTD., Shanghai (CN)

(72) Inventors: Chenghai Zhang, Shanghai (CN); Lingqiao Zhu, Shanghai (CN); Jinlin Guo, Shanghai (CN); Jie Zhao, Shanghai (CN); Honghai Gao, Shanghai (CN); Lin Ma, Shanghai (CN); Wei Dang, Shanghai (CN); Yan Yang, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 49 days.

(21) Appl. No.: 16/309,072

(22) PCT Filed: Jun. 9, 2017

(86) PCT No.: PCT/CN2017/087733
§ 371 (c)(1),
(2) Date: Dec. 11, 2018

(87) PCT Pub. No.: WO2017/215524
PCT Pub. Date: Dec. 21, 2017

(65) Prior Publication Data
US 2019/0161544 A1 May 30, 2019

(30) Foreign Application Priority Data

Jun. 12, 2016 (CN) .......................... 2016 1 0405511

(51) Int. Cl.
| | |
|---|---|
| *A61K 39/395* | (2006.01) |
| *C07K 16/24* | (2006.01) |
| *A61P 17/00* | (2006.01) |
| *A61P 25/00* | (2006.01) |
| *A61P 17/06* | (2006.01) |
| *A61P 27/02* | (2006.01) |
| *A61P 37/02* | (2006.01) |
| *A61P 29/00* | (2006.01) |
| *A61P 19/02* | (2006.01) |
| *A61P 11/06* | (2006.01) |
| *A61P 19/08* | (2006.01) |
| *A61P 37/06* | (2006.01) |
| *C12N 15/85* | (2006.01) |
| *A61K 38/00* | (2006.01) |

(52) U.S. Cl.
CPC .......... *C07K 16/244* (2013.01); *A61K 39/395* (2013.01); *A61P 11/06* (2018.01); *A61P 17/00* (2018.01); *A61P 17/06* (2018.01); *A61P 19/02* (2018.01); *A61P 19/08* (2018.01); *A61P 25/00* (2018.01); *A61P 27/02* (2018.01); *A61P 29/00* (2018.01); *A61P 37/02* (2018.01); *A61P 37/06* (2018.01); *C07K 16/24* (2013.01); *C12N 15/85* (2013.01); *A61K 38/00* (2013.01); *C07K 2317/51* (2013.01); *C07K 2317/565* (2013.01); *C12N 2015/8518* (2013.01)

(58) Field of Classification Search
None
See application file for complete search history.

(56) References Cited

PUBLICATIONS

Khan et al. Regulation of IL-17 in autoimmune diseases by transcriptional factors and microRNAs. Front Genet. Jul. 14, 2015;6:236.*
Bartlett et al. Targeting the IL-17-T(H)17 pathway. Nat Rev Drug Discov. Jan. 2015;14(1):11-2.*

* cited by examiner

*Primary Examiner* — Dong Jiang
(74) *Attorney, Agent, or Firm* — Greer, Burns & Crain, Ltd.

(57) ABSTRACT

An anti-human IL-17A monoclonal antibody, the preparation method, and the use thereof are provided. The anti-human IL-17A monoclonal antibody can specifically bind to human IL-17A and has a good effect for inhibiting the secretion of inflammatory cytokines, such as IL-6 and the like by means of various cell lines induced by IL-17A, and can be used for preparing drugs for treating diseases involving immune-medicated inflammatory responses.

13 Claims, 1 Drawing Sheet
Specification includes a Sequence Listing.

SEQUENCE LISTING

```
<160> NUMBER OF SEQ ID NOS: 20

<210> SEQ ID NO 1
<211> LENGTH: 345
<212> TYPE: DNA
<213> ORGANISM: Artificial
<220> FEATURE:
<223> OTHER INFORMATION: Nucleotide sequence encoding heavy chain
      variable region of anti-human IL-17A monoclonal antibody

<400> SEQUENCE: 1
gaagtgaaac tggtggaaag cggcggcggc ctggtgcgcc cgggcggcac cctgaaactg      60
agctgcgcgg cgagcggctt tacctttagc agctttgata tgagctgggg ccgccagacc     120
ccggaaaaac gcctggaatg ggtggcgttt atgagcagcg gcggcagcac ctattatccg     180
gatagcgtga aaggccgctt taccattagc cgcgataacg tgcgcaacat tctgtatctg     240
cagatgatta gcctgcgcag cgaagatacc gcgatgtatt attgcgcgcg cggcgaacgc     300
tatggcagct attggggcca gggcaccctg gtgaccgtga gcgcg                     345

<210> SEQ ID NO 2
<211> LENGTH: 115
<212> TYPE: PRT
<213> ORGANISM: Artificial
<220> FEATURE:
<223> OTHER INFORMATION: Amino acid sequence of heavy chain variable
      region of anti-human IL-17A monoclonal antibody

<400> SEQUENCE: 2

Glu Val Lys Leu Val Glu Ser Gly Gly Gly Leu Val Arg Pro Gly Gly
 1               5                  10                  15

Thr Leu Lys Leu Ser Cys Ala Ala Ser Gly Phe Thr Phe Ser Ser Phe
            20                  25                  30
```

```
Asp Met Ser Trp Gly Arg Gln Thr Pro Glu Lys Arg Leu Glu Trp Val
         35                  40                  45

Ala Phe Met Ser Ser Gly Gly Ser Thr Tyr Tyr Pro Asp Ser Val Lys
 50                  55                  60

Gly Arg Phe Thr Ile Ser Arg Asp Asn Val Arg Asn Ile Leu Tyr Leu
 65                  70                  75                  80

Gln Met Ile Ser Leu Arg Ser Glu Asp Thr Ala Met Tyr Tyr Cys Ala
                 85                  90                  95

Arg Gly Glu Arg Tyr Gly Ser Tyr Trp Gly Gln Gly Thr Leu Val Thr
            100                 105                 110

Val Ser Ala
        115

<210> SEQ ID NO 3
<211> LENGTH: 321
<212> TYPE: DNA
<213> ORGANISM: Artificial
<220> FEATURE:
<223> OTHER INFORMATION: Nucleotide sequence encoding light chain
      variable region of anti-human IL-17A monoclonal antibody

<400> SEQUENCE: 3
gatattcaga tgacccagag cagcagctat ctgagcgtga gcctgggcgg ccgcgtgacc     60
attacctgca aagcgagcga tcatattaac aactggctgg cgtggtatca gcagaaaccg   120
ggcaacgcgc cgcgcctgct gattagcggc gcgaccagcc tggaaaccgg cgtgccgagc   180
cgctttagcg gcagcggcag cggcaaagat tatacccctg acattaccag cctgcagacc   240
gaagatgtgg cgacctatta ttgccagcag tattggagca ccccgtttac ctttggcagc   300
ggcaccaaac tggaaattaa a                                             321

<210> SEQ ID NO 4
<211> LENGTH: 107
<212> TYPE: PRT
<213> ORGANISM: Artificial
<220> FEATURE:
<223> OTHER INFORMATION: Amino acid sequence of light chain variable
      region of anti-human IL-17A monoclonal antibody

<400> SEQUENCE: 4

Asp Ile Gln Met Thr Gln Ser Ser Ser Tyr Leu Ser Val Ser Leu Gly
 1               5                  10                  15

Gly Arg Val Thr Ile Thr Cys Lys Ala Ser Asp His Ile Asn Asn Trp
             20                  25                  30

Leu Ala Trp Tyr Gln Gln Lys Pro Gly Asn Ala Pro Arg Leu Leu Ile
         35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Thr Pro Phe
                 85                  90                  95

Thr Phe Gly Ser Gly Thr Lys Leu Glu Ile Lys
            100                 105

<210> SEQ ID NO 5
<211> LENGTH: 5
<212> TYPE: PRT
<213> ORGANISM: Artificial
<220> FEATURE:
```

-continued

<223> OTHER INFORMATION: Amino acid sequence of heavy chain
      complementarity determining region CDR1 of anti-human IL-17A
      monoclonal antibody

<400> SEQUENCE: 5

Ser Phe Asp Met Ser
1               5

<210> SEQ ID NO 6
<211> LENGTH: 16
<212> TYPE: PRT
<213> ORGANISM: Artificial
<220> FEATURE:
<223> OTHER INFORMATION: Amino acid sequence of heavy chain
      complementarity determining region CDR2 of anti-human IL-17A
      monoclonal antibody

<400> SEQUENCE: 6

Phe Met Ser Ser Gly Gly Ser Thr Tyr Tyr Pro Asp Ser Val Lys Gly
1               5                   10                  15

<210> SEQ ID NO 7
<211> LENGTH: 7
<212> TYPE: PRT
<213> ORGANISM: Artificial
<220> FEATURE:
<223> OTHER INFORMATION: Amino acid sequence of heavy chain
      complementarity determining region CDR3 of anti-human IL-17A
      monoclonal antibody

<400> SEQUENCE: 7

Gly Glu Arg Tyr Gly Ser Tyr
1               5

<210> SEQ ID NO 8
<211> LENGTH: 11
<212> TYPE: PRT
<213> ORGANISM: Artificial
<220> FEATURE:
<223> OTHER INFORMATION: Amino acid sequence of light chain
      complementarity determining region CDR1' of anti-human IL-17A
      monoclonal antibody

<400> SEQUENCE: 8

Lys Ala Ser Asp His Ile Asn Asn Trp Leu Ala
1               5                   10

<210> SEQ ID NO 9
<211> LENGTH: 7
<212> TYPE: PRT
<213> ORGANISM: Artificial
<220> FEATURE:
<223> OTHER INFORMATION: Amino acid sequence of light chain
      complementarity determining region CDR2' of anti-human IL-17A
      monoclonal antibody

<400> SEQUENCE: 9

Gly Ala Thr Ser Leu Glu Thr
1               5

<210> SEQ ID NO 10
<211> LENGTH: 9
<212> TYPE: PRT
<213> ORGANISM: Artificial
<220> FEATURE:
<223> OTHER INFORMATION: Amino acid sequence of light chain
      complementarity determining region CDR3' of anti-human IL-17A
      monoclonal antibody

<400> SEQUENCE: 10

Gln Gln Tyr Trp Ser Thr Pro Phe Thr
1               5

<210> SEQ ID NO 11
<211> LENGTH: 345
<212> TYPE: DNA
<213> ORGANISM: Artificial
<220> FEATURE:
<223> OTHER INFORMATION: Nucleotide sequence encoding heavy chain
      variable region of humanized anti-human IL-17A monoclonal antibody

<400> SEQUENCE: 11

```
gaagtgcagc tggtggaaag cggcggcggc ctggtgcagc cgggcggcag cctgcgcctg      60
agctgcgcgg cgagcggctt tacctttagc agctttgata tgagctgggg ccgccaggcg     120
ccgggcaaac gcctggaatg ggtggcgttt atgagcagcg gcggcagcac ctattatccg     180
gatagcgtga aaggccgctt taccattagc cgcgataaca gcaaaaacac cctgtatctg     240
cagatgaaca gcctgcgcgc ggaagatacc gcggtgtatt attgcgcgcg cggcgaacgc     300
tatggcagct attggggcca gggcaccctg gtgaccgtga gcagc                    345
```

<210> SEQ ID NO 12
<211> LENGTH: 115
<212> TYPE: PRT
<213> ORGANISM: Artificial
<220> FEATURE:
<223> OTHER INFORMATION: Amino acid sequence of heavy chain variable
      region of humanized anti-human IL-17A monoclonal antibody

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asp Met Ser Trp Gly Arg Gln Ala Pro Gly Lys Arg Leu Glu Trp Val
        35                  40                  45

Ala Phe Met Ser Ser Gly Gly Ser Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Arg Tyr Gly Ser Tyr Trp Gly Gln Gly Thr Leu Val Thr
            100                 105                 110

Val Ser Ser
        115

<210> SEQ ID NO 13
<211> LENGTH: 321
<212> TYPE: DNA
<213> ORGANISM: Artificial
<220> FEATURE:
<223> OTHER INFORMATION: Nucleotide sequence encoding light chain
      variable region of humanized anti-human IL-17A monoclonal antibody

<400> SEQUENCE: 13

```
gatattcaga tgacccagag cccgagcagc ctgagcgcga gcgtgggcga tcgcgtgacc      60
attacctgca aagcgagcga tcatattaac aactggctgg cgtggtatca gcagaaaccg     120
ggcaaagcgc cgaaactgct gattagcggc gcgaccagcc tggaaaccgg cgtgccgagc     180
```

```
cgctttagcg gcagcggcag cggcaccgat tatacccctga ccattagcag cctgcagccg    240
gaagattttg cgacctatta ttgccagcag tattggagca ccccgtttac ctttggcagc    300
ggcaccaaac tggaaattaa a                                              321
```

<210> SEQ ID NO 14
<211> LENGTH: 107
<212> TYPE: PRT
<213> ORGANISM: Artificial
<220> FEATURE:
<223> OTHER INFORMATION: Amino acid sequence of light chain variable
      region of humanized anti-human IL-17A monoclonal antibody

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105
```

<210> SEQ ID NO 15
<211> LENGTH: 445
<212> TYPE: PRT
<213> ORGANISM: Artificial
<220> FEATURE:
<223> OTHER INFORMATION: Amino acid sequence of heavy chain of humanized
      anti-human IL-17A monoclonal antibody

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asp Met Ser Trp Gly Arg Gln Ala Pro Gly Lys Arg Leu Glu Trp Val
        35                  40                  45

Ala Phe Met Ser Ser Gly Gly Ser Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Arg Tyr Gly Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 16
<211> LENGTH: 214
<212> TYPE: PRT
<213> ORGANISM: Artificial
<220> FEATURE:
<223> OTHER INFORMATION: Amino acid sequence of light chain of humanized
      anti-human IL-17A monoclonal antibody

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
```

```
        65                  70                  75                  80
Glu Asp Phe Ala Thr Tyr Tyr Cys Gln Gln Tyr Trp Ser Thr Pro Phe
                    85                  90                  95

Thr Phe Gly Ser Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 17
<211> LENGTH: 345
<212> TYPE: DNA
<213> ORGANISM: Artificial
<220> FEATURE:
<223> OTHER INFORMATION: Optimized nucleotide sequence encoding heavy
      chain variable region of anti-human IL-17A monoclonal antibody

<400> SEQUENCE: 17
gaagtgaagc tggtggagtc tgggggaggc ttagtgaggc ctggagggac cctgaaactc       60
tcctgtgcag cctctggatt cactttcagt agctttgaca tgtcttgggg tcgccagact      120
ccagaaaaga ggctggagtg gtcgcattt atgagtagtg gtggtagcac ctactatcca       180
gacagtgtga agggccgatt caccatctcc agagataatg tcaggaacat cctgtacctt      240
caaatgatca gtctgaggtc tgaggacacg gccatgtatt actgtgcaag aggcgaaagg      300
tacgggtctt actggggcca aggactctg gtcactgtct ctgca                       345
```

```
<210> SEQ ID NO 18
<211> LENGTH: 321
<212> TYPE: DNA
<213> ORGANISM: Artificial
<220> FEATURE:
<223> OTHER INFORMATION: Optimized nucleotide sequence encoding light
      chain variable region of anti-human IL-17A monoclonal antibody

<400> SEQUENCE: 18
gacatccaga tgacacaatc ttcatcctac ttgtctgttt ctctaggagg cagagtcacc       60
attacttgca aggcaagtga ccacattaat aattggttag cctggtatca gcagaaacca      120
ggaaatgcgc ctaggctctt aatatctggt gcaaccagtt tggaaactgg ggttccttca      180
agattcagtg gcagtggatc tgggaaggat tacactctca gcattaccag tcttcagact      240
gaagatgttg ctacttatta ctgtcaacag tattggagta ctccattcac gttcggctcg      300
gggacaaagt tggaaataaa a                                                321
```

```
<210> SEQ ID NO 19
<211> LENGTH: 345
<212> TYPE: DNA
```

```
<213> ORGANISM: artificial
<220> FEATURE:
<223> OTHER INFORMATION: Optimized nucleotide sequence encoding heavy
      chain variable region of humanized anti-human IL-17A monoclonal
      antibody

<400> SEQUENCE: 19
gaggtgcagc tcgtcgaatc tggaggcggc ctcgtgcagc ctgggggggtc tcttagattg      60 tcctgcgcag cttcaggatt cactttctcc agcttcgaca tgagctgggg gaggcaggct     120
ccagggaaga ggctggagtg ggtcgccttt atgtcctccg gaggcagtac atactacccc     180
gatagtgtga aagggaggtt taccatcagc cgcgacaaca gcaagaacac cctgtacctg     240
cagatgaata gcctgcgggc cgaggataca gccgtctact actgtgcccg gggcgagcgg     300
tacggctcct attggggcca agggacactg gtgactgtga gcagc                     345

<210> SEQ ID NO 20
<211> LENGTH: 321
<212> TYPE: DNA
<213> ORGANISM: Artificial
<220> FEATURE:
<223> OTHER INFORMATION: Optimized nucleotide sequence encoding light
      chain variable region of humanized anti-human IL-17A monoclonal
      antibody

<400> SEQUENCE: 20
gatattcaga tgacccagag cccaagcagc ctgtccgcat ctgtcggaga tagggtgact      60
atcacctgca aggcttccga ccacatcaac aattggctcg cctggtacca gcagaagcct     120
ggaaaggccc ctaagttgct catctccggc gccacatctc ttgaaaccgg ggtgccaagt     180 cggtttcag ggagtggcag cgggactgac tatacactga caatttcctc cctgcaaccc      240
gaggacttcg ccacatacta ctgtcagcag tactggagca cacctttac tttcgggagc     300 ggcaccaaac tggagattaa g                                               321
```

ANTI-HUMAN INTERLEUKIN-17A MONOCLONAL ANTIBODY

REFERENCE TO AN ELECTRONIC SEQUENCE LISTING

The contents of the electronic sequence listing (13B5526.txt; Size: 17.2 KB; and Date of Creation: Dec. 10, 2018) is herein incorporated by reference in its entirety.

BACKGROUND

The present invention relates to the field of antibodies, and particularly to an anti-human interleukin-17A monoclonal antibody, the preparation method and use thereof.

Interleukin 17 (IL-17) is an inflammatory cytokine secreted mainly by T helper 17 cells (Th17), and other T cells and innate immune cells such as mast cells and neutrophils can also secrete a certain amount of IL-17. It plays an important role in the pathological process of various inflammatory reactions and autoimmune diseases. The members of the IL-17 family include IL-17A, IL-17F, IL-17B, and IL-17C, IL-17 D in a homodimer form and IL-17A/F, IL-17E/IL-25 in a heterodimer form. In addition, there are two unnamed members. The IL-17 receptor (IL-17R) family includes IL-17RA, IL-17RB, IL-17RC, IL-17RD and IL-17RE, in which the homodimer IL-17A, together with the homodimer IL-17F and the heterodimer IL-17A/F, act on IL-17RA and IL-17RC. In vitro, the naive T cells are activated by stimulating with antigens and costimulatory molecules, the cytokines including transforming growth factor β (TGF-β), IL-6, IL-23 induce the differentiation of Th17, and Th17 cells secretcytokines IL-17A and IL-17F. IL-17/IL-17R complex participates in inflammatory response by activating the downstream signaling pathways such as NF-κB, c-jun N-terminal kinase (JNK) with the signal transduction complex IL-17R-Act1-TNF receptor associated factor 6 (TRAF6).

Studies have shown that IL-17 is fully involved in the pathological reactions of autoimmune diseases [Nature Reviews Drug Discovery, 2012. 11(10): 763-776]: IL-17 stimulates endothelial cells to secrete tissue factors, and promotes thrombosis; meanwhile, induces the secretion of inflammatory cytokines IL-6 and IL-8 from endothelial cells, epithelial cells, fibroblasts, macrophages and dendritic cells, and induces the occurrence of inflammatory reactions; acts on chondrocytes and then upregulates the expression of nitric oxide, resulting in cartilage destruction; meanwhile, induces osteoblasts to secrete the receptor activator of nuclear factor κ-B ligand (RANKL), promotes osteolysis and leads to bone injury.

Autoimmune diseases are caused by the tissue damage provoked by the body's autoimmune response to the autoantigen, including rheumatoid arthritis, ankylosing spondylitis, lupus erythematosus, psoriasis, and the like. Since the patients need treatment for a lifetime, and there is currently no cure for such a disease, it is known as "undead cancer", of which the incidence in population is about 3%. Autoimmune diseases will affect the central nervous system, lung, liver, kidney and other organs, leading to degeneration or even failure of the organ functions, such that the patients are not able to work or move, and ultimately their lives are threatened. In China, about 30-40 million people suffer from autoimmune diseases, and the current treatment drugs commonly used in China cannot meet the needs of the patients. Therefore, it is very urgent to develop an effective treatment with low toxicity and side effect for these patients.

Studies in recent years have shown that inflammatory cytokines such as tumor necrosis factor (TNF)-α, IL-6, and IL-17A fully mediate the occurrence and development of autoimmune diseases, and biological preparations antagonizing the inflammatory cytokines have gradually become the main treatment of autoimmune diseases. Anti-TNF-α antibody (Humira), which is specially used in the treatment of various autoimmune diseases, has been the world's best-selling drug for two consecutive years, with sales of $12.5 billion in 2014, and anti-IL-6 receptor antibody drug ACTEMRA has also been clinically used in the treatment of rheumatoid arthritis for many years. On the other hand, still more than ⅓ patients with rheumatoid arthritis on which TNF inhibitors has the most significant treatment effect do not respond to such preparations or develop drug resistance mechanisms. Meanwhile, it is very likely that the major inflammatory cytokines of autoimmune diseases differ greatly from each other: skin tissue biopsy results from the patients with autoimmune diseases show high expression levels of cytokines IL-17, IL-6 and IL-23, IL-22 in the tissues. Meanwhile, a large number of Th17 cells are found in the patient's blood and diseased skin, which is positively correlated with the progression of the diseases [Nature Reviews Drug Discovery. 2012, 11: 763-776]. In view of the fact that the secretion of inflammatory cytokines IL-6 and chemokine CXCL1 is probably the result of activation of IL-17 signaling pathway [Nature Immunology. 2007, 8: 247-256], targeting IL-17 may be one of the strategies for the treatment of autoimmune diseases. There is evidence that drug molecules targeting the IL-17A signaling pathway can effectively prevent the progression of autoimmune diseases [The New England Journal of Medicine. 2014, 371: 326-338; Nature Review Drug Discovery. 2012, 11: 763-776].

In conclusion, the development of efficient and specific IL-17A blocking antibody for blocking IL-17A signaling pathway will provide a new choice for the treatment of autoimmune diseases. The characteristics of autoimmune diseases which are chronic and difficult to cure determine that the patients need long-teen medication. However, the complex production process of antibody drugs makes the average price of macromolecular drugs much higher than that of small molecular drugs. Therefore, the development of drugs with higher biological activity will reduce the dosage, as well as the cost of medication, and improve the availability of the drugs. Screening and obtaining anti-IL-17A antibodies with higher biological activity has been an urgent problem to be solved by the person skilled in this art.

SUMMARY

In order to solve the above problems, the present invention provides a monoclonal antibody, namely recombinant anti-human IL-17A monoclonal antibody, that blocks IL-17A signaling by specifically blocking the binding of IL-17A to IL-17 receptor on cell surface and has a higher efficiency on blocking the IL-17A-mediated biological activity.

Thus, the first object of the invention is to provide an anti-human IL-17A monoclonal antibody.

The second object of the present invention is to provide a nucleotide molecule encoding the anti-human IL-17A monoclonal antibody.

The third object of the present invention is to provide an expression vector comprising the nucleotide molecule.

The fourth object of the present invention is to provide a host cell comprising the expression vector.

The fifth object of the present invention is to provide a method of preparing the anti-human IL-17A monoclonal antibody.

The sixth object of the present invention is to provide a composition comprising the anti-human IL-17A monoclonal antibody.

The seventh object of the present invention is to provide the use of the anti-human IL-17A monoclonal antibody.

In order to achieve the above objects, the present invention provides the following technical solutions:

The first aspect of the invention provides an anti-human IL-17A monoclonal antibody, which comprises: (1) a heavy chain complementarity determining region CDR1, CDR2, CDR3, wherein the CDR1 has the amino acid sequence as shown in SEQ ID NO: 5, the CDR2 has the amino acid sequence as shown in SEQ ID NO: 6, and the CDR3 has the amino acid sequence as shown in SEQ ID NO: 7; and (2) a light chain complementarity determining region CDR1', CDR2', CDR3', wherein the CDR1' has the amino acid sequence as shown in SEQ ID NO: 8, the CDR2' has the amino acid sequence as shown in SEQ ID NO: 9, and the CDR3' has the amino acid sequence as shown in SEQ ID NO: 10.

Preferably, the anti-human IL-17A monoclonal antibody comprises a heavy chain variable region having the amino acid sequence as shown in SEQ ID NO: 2, and a light chain variable region having the amino acid sequence as shown in SEQ ID NO: 4.

Preferably, the anti-human IL-17A monoclonal antibody is a humanized anti-human IL-17A monoclonal antibody, which comprises a heavy chain variable region having the amino acid sequence as shown in SEQ ID NO: 12, and a light chain variable region having the amino acid sequence as shown in SEQ ID NO: 14.

Preferably, the anti-human IL-17A monoclonal antibody comprises a heavy chain having the amino acid sequence as shown in SEQ ID NO: 15, and a light chain having the amino acid sequence as shown in SEQ ID NO: 16.

The second aspect of the invention provides a nucleotide molecule, which encodes the above-mentioned anti-human IL-17A monoclonal antibody.

Preferably, the nucleotide sequence encoding the heavy chain variable region of the anti-human IL-17A monoclonal antibody is as shown in SEQ ID NO: 1, and the nucleotide sequence encoding the light chain variable region is as shown in SEQ ID NO: 3.

More preferably, the nucleotide sequence encoding the heavy chain variable region of the anti-human IL-17A monoclonal antibody is as shown in SEQ ID NO: 17, and the nucleotide sequence encoding the light chain variable region is as shown in SEQ ID NO: 18.

Preferably, the nucleotide sequence encoding the heavy chain variable region of the anti-human IL-17A monoclonal antibody is as shown in SEQ ID NO: 11, and the nucleotide sequence encoding the light chain variable region is as shown in SEQ ID NO: 13.

More preferably, the nucleotide sequence encoding the heavy chain variable region of the anti-human IL-17A monoclonal antibody is as shown in SEQ ID NO: 19, and the nucleotide sequence encoding the light chain variable region is as shown in SEQ ID NO: 20.

The third aspect of the present invention provides an expression vector, and the expression vector comprises the above-mentioned nucleotide molecule.

Preferably, the expression vector is pDR1, pcDNA3.1(+), pDHFR or pCHO 1.0.

More preferably, the expression vector is pCHO 1.0.

The forth aspect of the present invention provides a host cell, and the host cell comprises the above-mentioned expression vector.

Preferably, the host cell is COS, CHO, NS0, sf9, sf21, DH5α, BL21 (DE3) or TG1.

More preferably, the host cell is CHO.

The fifth aspect of the present invention provides a method of preparing the above-mentioned anti-human IL-17A monoclonal antibody, and the method comprises the following steps of:

a) under expression conditions, cultivating the above-mentioned host cell to express the anti-human IL-17A monoclonal antibody;

b) isolating and purifying the anti-human IL-17A monoclonal antibody of step a).

The sixth aspect of the present invention provides a composition, and the composition comprises the above-mentioned anti-human IL-17A monoclonal antibody and a pharmaceutically acceptable carrier.

The seventh aspect of the present invention provides the use of the above-mentioned anti-human IL-17A monoclonal antibody and composition thereof for preparing drugs treating immune-mediated inflammatory responses.

Preferably, the immune-mediated inflammatory responses include one or more diseases selected from the group consisting of psoriasis, rheumatoid arthritis, psoriatic arthritis, ankylosing spondylitis, multiple sclerosis, asthma, uveitis, Behcet's uveitis, dry eye, and chronic idiopathic urticaria.

Beneficial Effect of the Invention

The anti-IL-17A monoclonal antibody of the invention can specifically bind to human IL-17A, and effectively inhibit IL-17A-induced secretion of inflammatory cytokines, such as IL-6, from various cell lines, therefore can be used to prepare drugs for treating diseases involving immune-mediated inflammatory responses.

DETAILED DESCRIPTION

In the present invention, any suitable expression vector can be used, which may be one of pDR1, pcDNA3.1(+), pDHFR and pCHO 1.0, and the expression vector includes a fusion DNA sequence to which a suitable transcriptional and translational regulatory sequence is ligated.

In the present invention, the host cell is a cell comprising the above expression vector, which can be a eukaryotic cell, such as mammalian or insect host cell culture system used for expression of the fusion protein of the present invention, COS, CHO (Chinese Hamster Ovary), NS0, sf9 and sf21 and the like; or can be a prokaryotic cell comprising the above expression vector, which may be one of DH5α, BL21 (DE3), and TG1.

Both the expression vector and the host cell used above are commercially available.

The method of preparing the anti-human IL-17A monoclonal antibody disclosed in the present invention comprises: culturing the above-mentioned host cell under expression conditions to express an anti-human IL-17A monoclonal antibody; isolating and purifying the anti-human IL-17A monoclonal antibody. Using the methods described above, the recombinant protein can be purified into homogenous substance, for example, showing a single band on SDS-PAGE electrophoresis.

The recombinant protein disclosed in the present invention can be isolated and purified by affinity chromatography method. According to the features of the affinity column used, conventional methods such as using high salt buffers and adjusting pH can be applied to elute fusion protein peptides that bind to the affinity column.

The humanized anti-human IL-17A monoclonal antibody disclosed in the present invention is obtained by following method: Balb/c mice were immunized with IL-17A antigen prepared in the laboratory. After immunization for several times, spleen cells of the mice with higher titer were selected and fused with hybridoma cells. The hybridoma cell strains having inhibitory activity on IL-17A function were screened. More specifically, by a large number of experiments, the inventors of the present invention first expressed IL-17A antigen and IL-17RA extracellular domain, respectively. On the basis of the experiments, mice were immunized with different adjuvants mixed with IL-17A antigen. Then spleen cells of the mice were further fused with hybridoma cell strains sp2/0, and the fused hybridomas were screened using IL-17A antigen to obtain positive cell strains. The target cell strains were obtained when the positive cell strains were verified to block the binding of IL-17A to IL-17R and indeed inhibit the function of IL-17A. After humanization of the target molecules, the light and heavy chain genes were simultaneously cloned into the eukaryotic expression vector pCHO 1.0. This expression vector was transfected into CHO cells by liposome method, and then positive cell clones were screened using puromycin and methotrexate. The highly expressed clones obtained by screening were cultured and expanded in a serum-free medium, and the humanized anti-human IL-17A monoclonal antibodies were isolated or purified using Protein A affinity column.

Further, conventional techniques in the field such as PCR mutagenesis may be used to further alter the murine parental antibody to produce chimeric, humanized or other variant forms of the antibody. The parental antibody of the invention can be mutagenized in, for example, the CDR structural domain to produce a variant antibody, which can be screened for the presence of a property of interest, such as binding affinity (lower KD), IC50, specificity; preferential binding, and the like. Preferably, the property of interest of the variant antibody is an improvement in properties relative to the parental antibody. The variant antibody is preferably replaced by an amino acid, and at least 1, 2, 3, 4, 5, 6, 7, 8, 9 or 10 amino acid residues of the parental antibody molecule are removed and a different residue is inserted in its position. The most interesting sites for substitution mutagenesis are one or more CDR regions, but FR changes are also contemplated. Conservative amino acid substitutions are preferred, and non-conservative amino acid changes can also be introduced and the property of interest can be screened using the obtained variant antibodies.

In vitro and in vivo biological experiments are carried out on the above anti-human IL-17A monoclonal antibody, and the results show that the antibody can bind well to IL-17A.

Specifically, various experiments including affinity detection, blocking experimental analysis of IL-17A binding to IL-17R, in vitro cell function detection and so on were performed on the above anti-human IL-17A monoclonal antibody. The experimental results show that the anti-human IL-17A monoclonal antibody of the present invention can bind to IL-17A secreted by cells, block the signal transmission between IL-17A and IL-17R, and inhibit the occurrence of inflammatory reaction. The above anti-human IL-17A monoclonal antibody of the present invention can be combined with a pharmaceutically acceptable carrier to form a pharmaceutical preparation composition which exerts a therapeutic effect more stably. And these preparations can ensure that the amino acid core sequence of the anti-human IL-17A monoclonal antibody of the present invention has an integrity conformation, and protect multifunctional groups of the protein from degradation (including but not limited to coagulation, deamination or oxidation). Typically, for the liquid preparation, it is stable for at least one year at 2° C. to 8° C., and for the lyophilized preparation, it is stable for at least six months at 30° C. The anti-human IL-17A monoclonal antibody preparation can be a preparation commonly used in the pharmaceutical field such as suspension, water needle, or lyophilized preparation, and preferably water needle or lyophilized preparation. For the water-needle or lyophilized preparation of the above anti-human IL-17A monoclonal antibody of the present invention, pharmaceutically acceptable excipients include, but not limited to, surfactants, solution stabilizers, isotonicity adjusting agents, buffers or a combination thereof. The surfactants include but not limited to, nonionic surfactants such as polyoxyethylene sorbitan fatty acid ester (Tween 20 or 80); poloxamer (e.g. poloxamer 188); Triton; sodium dodecyl sulfate (SDS), sodium lauryl sulfate; tetradecyl, linoleyl or octadecylsarcosine; Pluronics; MONAQUAT™, etc. And the surfactants are added in an amount such that the granulation tendency of the anti-human IL-17A monoclonal antibody is minimized. The solution stabilizers include but not limited to, one of the following: sugars, for example, reducing sugars and non-reducing sugars; amino acids, for example, monosodium glutamate or histidine; alcohols, for example, triols, higher sugar alcohols, propylene glycol, polyethylene glycol and the like, or a combination thereof. The solution stabilizer should be added in an amount such that the final formed preparation remains stable for a period of time that is considered stable by those skilled in the art. Isotonicity adjusting agents include but not limited to, one of sodium chloride, mannitol, or a combination thereof. The buffers include but not limited to, one of Tris, histidine buffer, phosphate buffer, or a combination thereof.

The above preparations are composition comprising the anti-human IL-17A monoclonal antibody, and after they are administrated to animals including human, the effect on anti-immune-mediated inflammatory responses is remarkable. Specifically they are effective for the prevention and/or treatment of immune-mediated inflammatory responses and can be used as anti-inflammatory drugs.

The immune-mediated inflammatory responses of the present invention mentioned include, but not limited to, psoriasis, rheumatoid arthritis, psoriatic arthritis, ankylosing spondylitis, multiple sclerosis, asthma, uveitis, Behcet's uveitis, dry eye, and chronic spontaneous urticaria. In addition to the above-mentioned inflammation-related diseases, the above preparation can also be used for treating multiple sclerosis, Crohn's disease, colitis, ulcerative colitis, systemic lupus erythematosus, graft-versus-host disease, and the like.

The anti-immune-mediated inflammatory response drugs of the present invention refers to inhibit and/or treat immune-mediated inflammatory responses, which may include the delay in the development of symptoms associated with immune-mediated inflammatory responses and/or the reduction in the severity these symptoms. It further includes the alleviation of symptoms associated with the inflammatory responses and the prevention of the other symptoms, as well as the reduction or prevention of metastasis of the inflammatory responses.

When the anti-human IL-17A monoclonal antibody and the composition thereof in the present invention are administered to animals including human, the dose varies depending on the age and weight of the patient, the characteristics and severity of the disease, and the administration route, which can refer to the results and various conditions of the animal experiment. The total dose cannot exceed a certain range. Specifically, the dose for intravenous injection is 1-1800 mg/day.

The following embodiments and experimental examples are intended to further illustrate the present invention and not to be construed as limiting the invention. The examples do not include detailed descriptions of conventional methods, such as those used to construct vectors and plasmids, the methods of inserting genes encoding proteins into the vectors and plasmids or methods of introducing the plasmids into host cells. Such methods are well known to those skilled in the art and are described in a number of publications, including Sambrook, J., Fritsch, E. F. And Maniais, T. (1989) Molecular Cloning: A Laboratory Manual, 2nd edition, Cold spring Harbor Laboratory Press.

Example 1

Preparation of IL-17A, Seckinumab, Ixekizumab and Soluble-IL-17RA Extracellular Domain The sequence of human IL-17A antigen was derived from Pubmed (NM_002190.2). The amino acid sequence of hIL-17A (hIL-17A-his-tag) containing a hexahistidine (his) tag at the C-terminus was supplied to Sangon Biotech company to perform codon optimization according to codon usage preference of *Cricetulusgriseus* and synthesize the gene fragment, which was then subcloned into the pUC57 vector (derived from Sangon Biotech company) to obtain pUC57-hIL-17A-histag. The hIL-17A-histag fragment was digested from the pUC57-hIL-17A-histag vector using the AvrII and EcoRV cleavage sites and constructed into the pCHO 1.0 expression vector (purchased from Life Technologies company) to obtain pCHO 1.0 (hIL-17A-histag). Then sequencing was performed, and clones with completely correct sequences were selected for transfection.

The pCHO 1.0 (hIL-17A-his-tag) vector was transfected into the CHO-S cell line (purchased from Life Technologies company) by liposome method, cultured in CD FortiCHO medium (purchased from Life Technologies company) containing 6 mM glutamine (purchased from Gibco company) for 2 days and then positive cell clones were screened with puromycin (purchased from Gene Operation company) and methotrexate (purchased from Sigma company). The $3 \times 10^5$ positive cell clones were inoculated into a 200 ml/1 L shake flask using CD FortiCHO medium containing 6 mM glutamine and 1/100 volume ratio of anti-aggregation reagent (purchased from Invitrogen company) as medium, and cultured for 12 days. The supernatant was collected and the hIL-17A-histag antigen was purified using a nickel column. Protein quantification was performed by the bicinchoninic acid (BCA) method. The protein obtained from purification was used for the following mouse immunization and further analysis.

The amino acid sequence of anti-IL-17A monoclonal antibody Secukinumab (IgG1, κ) published by who.int (see WHO Drug information Vol. 23, No. 4, 2009. P342) was subjected to codon optimization and whole gene synthesis to obtain a nucleotide sequence, cloned into pCHO 1.0 expression vector, and sequenced to confirm that the correct cloning vector was obtained, designated as pCHO 1.0 (Secukinumab). The pCHO 1.0 (Secukinumab) vector was transiently transfected into the CHO-S cell line, cultured for several days in CD FortiCHO medium containing 6 mM glutamine, and then the positive antibody protein was purified from the cell culture supernatant using Protein A affinity chromatography column (purchased from Pharmacia company).

The amino acid sequence of Ixekizumab (IgG4, κ) derived from who.int (see WHO Drug Information Vol. 25, No. 2, 2011. P176) was also cloned into the pCHO 1.0 expression vector, and transiently transferred to the CHO-S cell line. The cells were cultured for several days in CD FortiCHO medium containing 6 mM glutamine, and then the cell culture supernatant was collected and purified using Protein A affinity chromatography column. The culture and purification conditions were identified with that of the above-mentioned Secukinumab.

The method of preparing soluble IL-17 receptor A-extracellular domain (IL-17RA-ECD)-Fc fusion protein was as follows: Using IL-17RA gene (purchased from Beijing Yiqiao Shenzhou Company) as a template, the N-terminal 1-288 nucleotide fragment was amplified by PCR, and linked to the human IgG1 constant region (Fc) fragment using glycine serine (GS) as an artificial linker. The constant region sequence of human IgG1 employed the constant region sequence of Secukinumb. The sequence was constructed into the pCHO 1.0 vector to obtain pCHO 1.0 (IL-17RA-ECD-Fc). Then, sequencing was performed, and clones with completely correct sequences were selected for stable transfection. Transfection and expression were performed according to the conditions of hIL-17-histag. IL-17RA-ECD-Fc was purified from the cell culture supernatant using Protein A affinity chromatography column.

Example 2

Immunization of IL-17A

The hIL-17A-histag antigen (50 μg/mouse) was diluted with physiological saline to 75 μl, mixed with an equal volume of Freund's complete adjuvant, fully ultrasonically emulsified, and then administrated to 4-5 weeks old Balb/c mice (purchased from Shanghai Lingchang Biotechnology Co., Ltd., animal production license number: SCXK (Shanghai) 2013-0018) by multipoint subcutaneous injection. Three weeks later, the same amount of protein was also diluted to 75 μl and mixed with an equal volume of Freund's incomplete adjuvant, fully phaco-emulsified, and then administrated to mice by multipoint subcutaneous immunization. Such immunization was repeated two weeks later. All mice were bled by tail to separate serum after one week of the third immunization, and serum titers were detected using an ELISA coated with hIL-17A-histag antigen. For the mice with serum antibody titers >10,000, the following immunization protocol was performed one week after blood collection: 10 μg, antigen protein/100 μl saline/mouse was injected into the tail vein.

Titer was determined using ELISA: hIL-17A-his-tag was used for coating the ELISA plate at a concentration of 2.5 μg/ml, 100 μl for each well, overnight at 4° C. The plate was washed twice with PBST (PBS containing 0.5% Tween-20) and patted dry. Each well was added with 200 µl of coating buffer containing 1% BSA, blocked at room temperature for 4 hours and patted dry, and stored in a refrigerator at −20° C. until use. When detection was performed, different concentrations of mouse serum were added to the ELISA plate with 100 µl per well. Two replicate wells were set up, and incubated at room temperature for 1.5 hours. The plate was washed 3 times with PBST and then patted dry. 100 µl of HRP-labeled rabbit anti-mouse Ig antibody (purchased from Sigma) diluted 1:10000 with PBST was added, and incubated for 1 hour at room temperature. The plate was washed 3 times with PBST and then patted dry. Each well was added with 100 µl of chromogenic solution (chromogenic solution A and chromogenic solution B of ELISA were mixed at a volume ratio of 1:1 before use) to develop color and then each well was added with 100 µl of 2M $H_2SO_4$ as stop solution to terminate the reaction. The OD value of each well was measured immediately at a wavelength of 450 nm using a microplate reader (Molecular Device).

Example 3

Hybridoma Fusion and Screening

The spleen cells of the mice were taken for fusion three days after the last immunization.

Sp2/0 myeloma cells (derived from the Cell Culture Bank of the Chinese Academy of Sciences) in good condition were cultured in a 37° C., 5% $CO_2$ incubator, and the medium was renewed one day prior to fusion. The fusion and screening process was as follows: Anesthetized mice were sacrificed by cervical dislocation; the spleens of the mice were taken out and ground into debris; spleen cells were collected, washed and counted. The two kinds of cells above mentioned were mixed in a ratio of spleen cells: sp2/0 cells=10:1, and centrifuged at 1500 rpm for 7 minutes. The supernatant was discarded. 1 ml of PEG (1450) was added in 1 minute and the mixture of cells was gently shaken for 90 seconds. 5 ml of serum-free DMEM (purchased from Gibco company) was added in 2.5 minutes, and then additional 5 ml of serum-free medium was added in one time to terminate the PEG-mediated cell fusion reaction. The sample was allowed to stand for 5 minutes, and centrifuged at 1280 rpm for 8 minutes. In a ratio of two million sp2/0 cells per 96-well plate, the cells in the sample were uniformly inoculated in a 96-well plate with 200 µl per well, and first screened with HAT medium containing hypoxanthine (H), aminopterin (A) and thymidine (T). The medium was half-renewed every 3-4 days and replaced by HT medium on the 10th day. After 10 days, when the hybridoma cells were spread over 10% of the bottom of the 96-well plate, the supernatant was taken for ELISA using a plate coated with hIL-17A-histag. The ELISA method was the same as above. Positive hybridoma clones were selected for expansion in 24-well plates and subcloned by limiting dilution. Monoclonal hybridoma strains stably expressing antibodies of interest were obtained and then cryopreserved.

Example 4

Blocking of IL-17A Binding to IL-17RA by Murine Anti-Human IL-17A Monoclonal Antibodies ELISA was used to study the blocking of IL-17A binding to IL-17RA by murine anti-IL-17A monoclonal antibodies. ELISA plates were coated with hIL-17A-his-tag and blocked, and then IL-17RA-ECD-Fc and 300 µl of subcloned hybridoma cell culture supernatant of murine anti-IL-17A monoclonal antibodies were mixed and added, and finally HRP-conjugated goat anti-human IgG antibody was added for chromogenic detection. The clones that could block the binding of IL-17A to IL-17RA-ECD-Fc were subjected to a next round of subcloning.

Example 5

Inhibition of IL-17A-Induced IL-6 Secretion from Hela Cells by Murine Anti-Human IL-17A Monoclonal Antibodies The hybridoma cell strains through three rounds of subcloning were expanded in serum-five medium, and then the supernatants were collected and subjected to antibody purification respectively using Protein G (purchased from GE company) affinity column. The concentrations of purified antibodies were quantified.

IL-17A recognizes the IL-17R on cell surface, and then induces the secretion of inflammatory cytokines including IL-6. This is the main pathogenic mechanism of IL-17A in autoimmune diseases. Therefore, the potency of anti-IL-17A antibodies neutralizing IL-17A was examined using Hela cells.

Hela cells in good condition (from the Cell Culture Bank of the Chinese Academy of Sciences) were treated with 15 ng/ml recombinant human IL-17A (purchased from R&D Systems) and various concentrations of murine anti-human IL-17A monoclonal antibodies. The culture medium was DMEM (purchased from Gibco) containing 10% fetal bovine serum (purchased from Sigma), 100 U/ml penicillin (purchased from Gibco) and 100 µg/ml streptomycin (purchased from Gibco). Four replicate wells were set up in each group, and the cell culture supernatants were collected after incubation at 37° C., 5% $CO_2$ for 24 hours. The IL-6 secretion by cells in each group was determined by ELISA.

The ELISA was performed as follows: A rat anti-human IL-6 antibody was used for coating ELISA plate (purchased from R&D Systems) at a concentration of 2.5 µg/ml, 100 µl per well, overnight at 4° C. The plate was washed twice with PBST and patted dry. Each well was added with 200 µl of coating buffer containing 1% BSA, and blocked at room temperature for 4 hours, patted dry, and stored in a refrigerator at −20° C. until use. When detection was performed, standardized human IL-6 was serially diluted at concentrations of 10 ng/ml, 3.3 ng/ml, 1.1 ng/ml, 370 pg/ml, 120 pg/ml, 41 pg/ml, 13 pg/ml and 4.6 pg/ml, respectively, and then transferred to the coated ELISA plate with 100 µl per well, and 2 replicate wells were set up for each concentration. Similarly, the cell supernatants were diluted twice with DMEM, and then transferred to the coated ELISA plate with 100 µl per well, and replicate wells were set up and incubated at room temperature for 1.5 hours. The plate was washed 3 times with PBST and then patted dry. 100 µl of biotinylated rat anti-human IL-6 (purchased from R&D Systems, diluted 1000-fold with PBST containing 1% BSA) was added to each well and incubated for 1 hour at room temperature. The plate was washed 3 times with PBST and patted dry. 100 µl of Streptavidin HRP (purchased from BD Pharmingen, diluted 1000-fold with PBST containing 1% BSA) was added to each well, and incubated for 1 hour at room temperature. 100 µl of chromogenic solution was added to each well (the ELISA chromogenic solution A and chromogenic solution B were mixed in a volume ratio of 1:1 before use), and then 100 µl of 2M $H_2SO_4$ as stop solution was added to each well to terminate the reaction. The OD value of each well was measured immediately at a wavelength of 450 nm using a microplate reader (Molecular Device).

After analyzing the functional activities of 10 murine anti-human IL-17A monoclonal antibodies on inhibiting IL-17A-induced IL-6 secretion from Hela cells, it was found that the potency of most antibodies evaluated were comparable to that of Secukinumab. Several antibodies were picked for further functional analysis. The No. 120 antibody exhibited an $IC_{50}$ value of 30.52 pM in the cell-based assay, while Secukinumab and Ixekizumab exhibited $IC_{50}$s of 108.70 pM and 60.60 pM, respectively. Therefore, the murine No. 120 antibody of the present invention has a stronger inhibitory effect on IL-17A than Secukinumab and Ixekizumab.

Example 6

Determination of Binding Kinetics and Affinities of Murine Anti-Human IL-17A Monoclonal Antibodies The binding kinetics and affinities of the murine anti-human IL-17A monoclonal antibodies to IL-17A were determined by Biacore T200 (GE healthcare), and Secukinumab and Ixekizumab were used as controls. The specific experimental method was as follows: Amine Coupling Kit (GE healthcare) was used to activate CM5 sensor chips (GE healthcare) and recombinant Protein A/G (Thermo Pierce) was immobilized on the chip with an amount of 2000 RU. FC3 (Flow cell 3) was a reference channel, and FC4 (Flow cell 4) was a sample channel. Murine 120 antibody or control antibodies were captured on the FC4 channel respectively, followed by injection of various concentrations of hIL-17A. The cycling conditions were as follows: the analyte was injected at 50 μl/min for 4 min in all channels of the FCs, the dissociation time was 20 min, and 6M guanidine hydrochloride (National Pharmaceutical Group Chemical Reagent Co., Ltd.) was injected at a rate of 10 μl/min for 30 s to surface regeneration. Then, difference between the signals of the captured antibodies and antibody-free controls were adopted to calculate binding kinetics and affinities using Biacore T200 Evaluation Software Ver 1.0.

The experiment results are shown in Table 1. The results indicate that the murine anti-human IL-17A monoclonal antibody of the present invention has a higher affinity for IL-17A than Secukinumab and Ixekizumab.

TABLE 1

Binding kinetics and affinities of murine anti-human IL-17A monoclonal antibody for human IL-17A

| Antibody | Ka (1/Ms) | Kd (1/s) | KD (pM) |
| --- | --- | --- | --- |
| 120 | $2.035 \times 10^5$ | $6.076 \times 10^{-8}$ | 0.299 |
| Ixekizumab | $5.151 \times 10^5$ | $3.28 \times 10^{-5}$ | 63.68 |
| Secukinumab | $2.65 \times 10^5$ | $3.16 \times 10^{-5}$ | 118 |

Example 7

Determination of the Sequence of Murine Anti-Human IL-17A Monoclonal Antibody

Total RNA of each hybridoma cell strain was extracted using Trizol (purchased from Sango Biotech (Shanghai)), and mRNA was reverse-transcribed into cDNA using a reverse transcription kit (purchased from Takara company). The genes of light chain variable region and heavy chain variable region of the murine anti-human IL-17A monoclonal antibody were amplified by PCR using Mouse Ig-Primer Set (purchased from Novagen company), and then the PCR products were cloned into the pMD18-T vector, and the variable region genes were sequenced and analyzed. Based on various functional experiments and sequence analysis results, we finally picked clone No. 120 as a lead antibody, and its sequence information is as follows: the heavy chain variable region gene sequence is 345 bp in length, encoding 115 amino acid residues, the nucleotide sequence is shown in SEQ ID NO: 1, the amino acid sequence is shown in SEQ ID NO: 2; the light chain variable region gene sequence is 321 bp in length, encoding 107 amino acid residues, and the nucleotide sequence is shown in SEQ ID NO: 3, and the amino acid sequence is shown in SEQ ID NO:4. The amino acid sequences were aligned in GenBank, both of them are consistent with the characteristics of the mouse IgG variable region gene.

Furthermore, by further codon-optimizing the sequences of above-mentioned heavy chain variable region gene and light chain variable region gene, the sequences are more compatible with the cell expression system. The nucleotide sequence of the optimized heavy chain variable region gene is shown in SEQ ID NO. 17, the nucleotide sequence of the optimized light chain variable region gene is shown in SEQ ID NO: 18.

Example 8

Humanization of Anti-Human IL-17A Monoclonal Antibody

Chimeric antibody (120-chimera, 120-Ch) was constructed by recombine the heavy chain variable region and the light chain variable region of murine antibody No. 120 with the heavy and light chain constant region of human IgG1 (derived from Secukinumab) by overlapping PCR, respectively.

Meanwhile, according to the Kabat rule, the amino acid sequences of the light chain variable region and the heavy chain variable region of the murine anti-human IL-17A monoclonal antibody No. 120 were analyzed and three complementarity determining regions (CDR) and four frame regions (FR) were identified, in which the amino acid sequences of the heavy chain complementarity determining region are CDR1:SFDMS (SEQ ID NO:5), CDR2: FMSSGGSTYYPDSVKG (SEQ ID NO:6) and CDR3: GERYGSY (SEQ ID NO:7); the amino acid sequences of the light chain complementarity determining region are CDR1':KASDHINNWLA (SEQ ID NO: 8), CDR2':GATSLET (SEQ ID NO: 9) and CDR3':QQYWSTPFT (SEQ ID NO: 10).

By homology comparison with human IgGgermline sequence at NCBI IgBlast, IGHV3-66*02 was selected as the heavy chain CDR graft template, and then the heavy chain CDR regions of murine anti-human IL-17A monoclonal antibody No. 120 were grafted into the IGHV3-66*02 framework region to construct a heavy chain CDR-grafted antibody. Similarly, by homology comparison with human IgGgermline sequence, IGKV1-NL1*01 was selected as the light chain CDR graft template, and the light chain CDR regions of murine anti-human IL-17A monoclonal antibody No. 120 were grafted into IGKV1-NL1*01 framework region to construct a light chain CDR-grafted antibody. The obtained antibody was defined as 120-Gr (120-Grafting). Meanwhile, on this basis, some amino acid sites in the framework region were subjected to back mutation. When back mutation was preformed, the amino acid sequence was encoded by Kabat numbering system and the position was indicated by Kabat numbering. Preferably, for the heavy chain variable region sequence, V at position 29 by Kabat numbering was back mutated to murine F, V at position 37 was mutated to G, G at position 44 was mutated to R, and S at position 49 was mutated to A. For the light chain variable region sequence, L at position 48 by Kabat numbering was mutated to I, and Y at position 49 was mutated to S. The above variable region gene sequences were codon-optimized and synthesized according to the codon usage preference of *Cricetulusgriseus* by Sango Biotech. The synthetic humanized variable region sequences were ligated to the human IgG1 constant region, and the antibody was defined as a humanized antibody of 120 (120-Humanization, 120-Hu).

At the same time, based on this antibody, we constructed other affinity matured humanized sequences, including: 120-Lc T69K (according to the Kabat numbering system, T at position 69 on the 120-Hu light chain was further returned to K); 120-Lc K45R (K at position 45 on the 120-Hu light chain was returned to R); 120-Lc K42N (K at position 42 on the 120-Hu light chain was returned to N) and 120-Hc K75R (K at position 75 on the heavy chain of 120-Hu was returned to R). The 120-Lc mutant sequence was combined with the 120-Hu heavy chain to form an antibody gene; and the 120-Hc mutant sequence was combined with the 120-Hu light chain to form an antibody gene.

The transient expression vectors of the humanized heavy and light chains were separately constructed using the pTT5 vector (purchased from NRC Biotechnology Research Institute), and the above light and heavy chain combinations were subjected to transient transfection and antibody expression by the HEK293 system (purchased from NRC Biotechnology Research Institute). HEK293 cells were cultured in Free Style 293 Expression Medium (purchased from Gibco company). The plasmid was transferred into cells by PEI transfection, and 5 days later, the cell supernatant was collected, and purified by Protein A to obtain the antibody.

Because 120-Hu has the highest degree of humanization among the five antibodies, it was used as the standard and the cell activities of the other four antibodies were compared with 120-Hu. The cell activities of the four antibodies were equal or weaker than that of 120-Hu. In order to maximize the humanization degree of the antibody of interest, we chose 120-Hu as the leader antibody molecule from these antibodies.

On this basis, in order to further increase the humanization degree of the antibody, we mutated each reverse mutation site back to human amino acid residue, respectively. For the heavy chain variable region sequence, F at position 29 by Kabat numbering of 120-Hu was returned to murine V; or G at position 37 was returned to V; or R at position 44 was returned to G; or A at position 49 was returned to S. Each heavy chain sequence having single point mutation was combined with the 120-Hu light chain gene to form an antibody gene. For the light chain variable region sequence, I at position 48 by Kabat numbering of 120-Hu was returned to L, or S at position 49 was returned to Y, respectively. Each light chain sequence having single point mutation was combined with the 120-Hu heavy chain gene to form an antibody gene.

By the same conditions as mentioned above, the antibody molecules were transiently transduced, expressed, and detected for cell activity. It was confirmed that all the antibodies having single-point mutation have lower activity than 120-Hu. Therefore, 120-Hu is the final target molecule as a suitable humanized antibody.

Finally, the humanized heavy chain variable region gene sequence of 120 is 345 bp in length, encoding 115 amino acid residues, the nucleotide sequence is shown in SEQ ID NO: 11, and the amino acid sequence is shown in SEQ ID NO: 12. The humanized light chain variable region gene sequence is 321 bp in length, encoding 107 amino acid residues, the nucleotide sequence is shown in SEQ ID NO: 13, and the amino acid sequence is shown in SEQ ID NO: 14. When ligated to the human IgG1 constant region, a humanized heavy chain of 120-Hu having 445 amino acids (with sequence as shown in SEQ ID NO: 15) and a humanized light chain of 120-Hu having 214 amino acids (with sequence as shown in SEQ ID NO: 16) were obtained.

Furthermore, by further codon-optimization of the sequences of the above-mentioned heavy chain variable region gene and light chain variable region gene, they are more compatible with the cell expression system. The optimized heavy chain variable region gene has the nucleotide sequence as shown in SEQ ID NO: 19, and the optimized light chain variable region gene has the nucleotide sequence as shown in SEQ ID NO: 20.

Example 9

Affinity of Humanized Anti-Human IL-17A Monoclonal Antibody for IL-17A

The affinity of the 120-Hu antibody was evaluated by Biacore (see Example 6). The results showed that the affinity of the humanized antibody 120-Hu for hIL-17A was 0.02 pM (see Table 2), which was much higher than that of Secukinumab and Ixekizumab. Since the limitation of detection of Biacore was at pM level, the affinity of 120-Hu exceeded the limitation, were corded it to be <1 pM.

TABLE 2

Affinity of 120-HuforIL-17A

| Antibody | Ka (1/Ms) | Kd (1/s) | KD (pM) |
|---|---|---|---|
| 120-Hu | $4.45 \times 10^5$ | $8.77 \times 10^{-9}$ | <1 pM |
| Ixekizumab | $2.30 \times 10^6$ | $9.45 \times 10^{-5}$ | 41.08 |
| Secukinumab | $2.65 \times 10^5$ | $3.16 \times 10^{-5}$ | 119.25 |

Example 10

Figure 1:
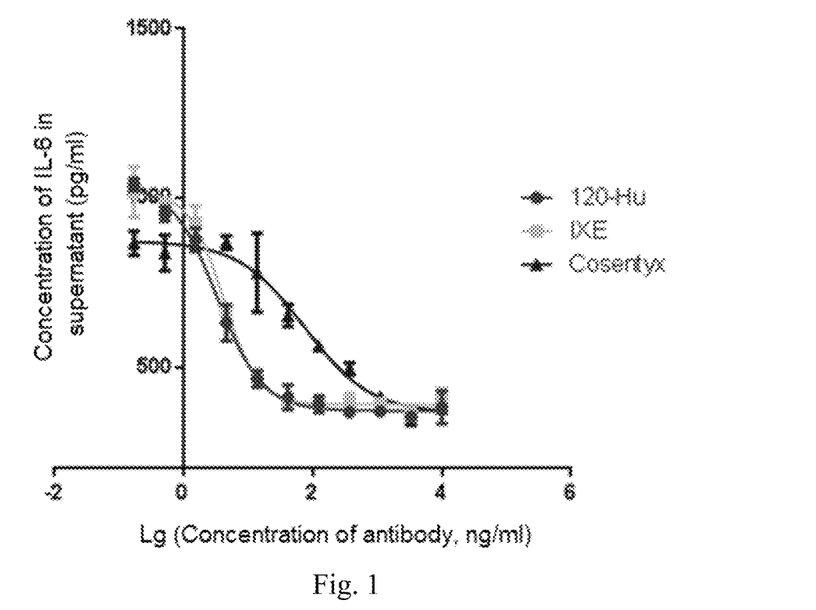
FIG. 1 shows the experiment results of blocking of human IL-17A-induced IL-6 secretion of Hela cells by the humanized anti-human IL-17A monoclonal antibody.

Inhibition of IL-17A-Induced IL-6 Secretion from Hela Cells by Humanized Anti-Human IL-17A Monoclonal Antibody Inhibition of hIL-17A-induced IL-6 secretion from HeLa cells by the humanized 120 antibody was detected (see Example 5 for experimental methods). Secukinumab (Consentyx) in this example was purchased from Novartis, and Ixekizumab was prepared according to Example 1. The results showed that the humanized antibody maintained relatively high biological activity, and multiple experiments confirmed that the activity of 120-Hu in vitro was stronger than that of Secukinumab ($p<0.05$, n=3) and Ixekizumab ($p<0.01$, n=3) (Table 3; representative experiment is shown in FIG. 1). In vitro biological activity of the antibody is one of the important factors determining the in vivo efficacy of the antibody. The ability of 120-Hu to strongly inhibit IL-17A function indicates that it will be a highly effective antibody candidate drug.

TABLE 3

Inhibition of IL-17A-induced IL-6 secretion from Hela cells by 120-Hu

| Antibody No./IC50(pM) | 120-Hu | Ixekizumab | Secukinumab |
| --- | --- | --- | --- |
| Experiment 1 | 14.73 | 21.85 | 913.33 |
| Experiment 2 | 21.99 | 27.43 | 495.67 |
| Experiment 3 | 44.59 | 50.67 | 738.67 |

Example 11

In Vivo Efficacy of Humanized Anti-Human IL-17A Monoclonal Antibody

Since 120-Hu does not recognize non-primate-derived IL-17A, we were unable to directly construct a relevant animal disease model using normal rodents to determine the efficacy of 120-Hu in the treatment of autoimmune diseases. By exogenously administering hIL-17A, we evaluated the inhibitory effect of 120-Hu on the cascade inflammatory response in mice.

In autoimmune diseases, IL-17A is induced to express at a high level, which recognizes IL-17R and activates a signaling pathway. The cascade induces cells to secret a large amount of chemokines and cytokines including CXCL1 (CXC motif ligand 1), thereby triggering an inflammatory response and attacking normal cells and organs of the body. Therefore, antagonizing IL-17A with an antibody will inhibit the occurrence of this response and prevent the progression of autoimmune diseases [World J Rheumatol. 2013; 3:25-31]. Human IL-17A can cross-react with mouse IL-17R and elicits a subsequent cascade response. Thus, by observing the inhibition of CXCL1 secretion of IL-17A-challenged mice will predict the efficacy of the antibody in the treatment of autoimmune diseases.

Figure 2:
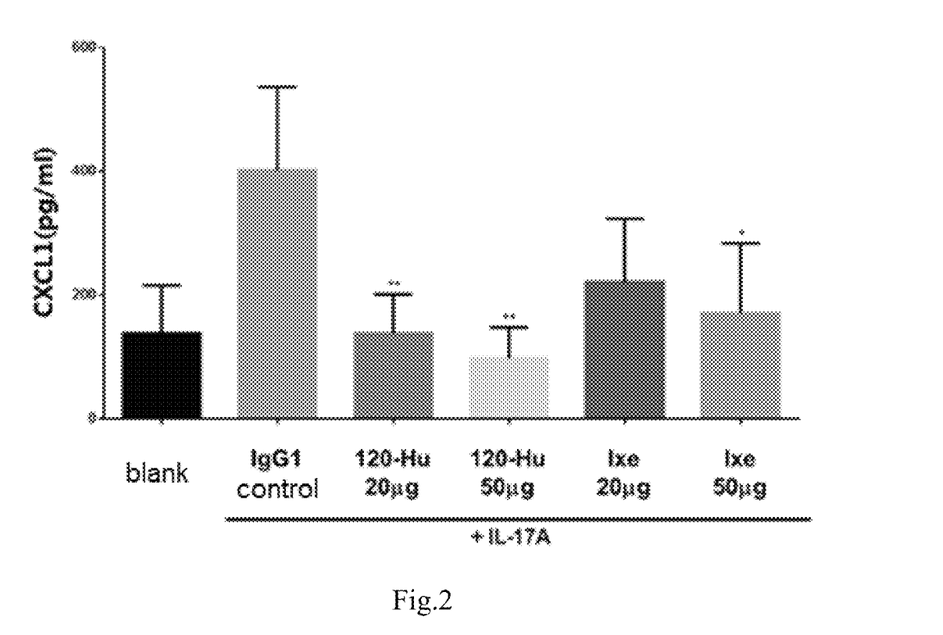
FIG. 2 shows the experiment results of inhibition of human IL-17A-induced CXCL1 secretion in mice by the humanized anti-human IL-17A monoclonal antibody.

5-8 weeks old male Kunming mice (purchased from Shanghai Lingchang Biotechnology Co., Ltd., animal production license number: SCXK (Shanghai) 2013-0018) were intraperitoneally injected with various dosages of antibodies (20 μg/mouse-50 μg/mouse) on the first day. After 24 hours, recombinant human IL-17A was subcutaneously injected (3 μg/mouse), and after 3 hours, the mice were sacrificed and blood was taken. The concentration of CXCL1 in the serum was measured using a murine CXCL1 ELISA assay kit (purchased from R&D Systems). In the experiment, IgG1 control antibody and Ixekizumab were used as negative and positive control, respectively. The results showed that 120-Huat lower dosage (20 μg/mouse) can significantly inhibit the IL-17A induced CXCL1 secretion, and 120-Hu is more effective to neutralize IL-17A in vivo than Ixekizumab at the same dosage (see FIG. 2).

What is claimed is:

1. An isolated anti-human IL-17A monoclonal antibody comprising:
   (1) a heavy chain variable region comprising CDR1, CDR2 and CDR3, wherein the CDR1 has the amino acid sequence of SEQ ID NO: 5, the CDR2 has the amino acid sequence of SEQ ID NO: 6, and the CDR3 has the amino acid sequence of SEQ ID NO: 7; and
   (2) a light chain variable region comprising CDR1', CDR2' and CDR3', wherein the CDR1' has the amino acid sequence of SEQ ID NO: 8, the CDR2' has the amino acid sequence of SEQ ID NO: 9, and the CDR3' has the amino acid sequence of SEQ ID NO: 10.

2. The anti-human IL-17A monoclonal antibody of claim 1, wherein the heavy chain variable region comprises the amino acid sequence of SEQ ID NO: 2, and the light chain variable region comprises the amino acid sequence of SEQ ID NO: 4.

3. The anti-human IL-17A monoclonal antibody of claim 1, wherein the heavy chain variable region comprises the amino acid sequence of SEQ ID NO: 12, and the light chain variable region comprises the amino acid sequence of SEQ ID NO: 14, and wherein the antibody is a humanized antibody.

4. The anti-human IL-17A monoclonal antibody of claim 3, comprising a heavy chain having the amino acid sequence of SEQ ID NO: 15, and a light chain having the amino acid sequence of SEQ ID NO: 16.

5. A composition, comprising the anti-human IL-17A monoclonal antibody of claim 1 and a pharmaceutically acceptable carrier.

6. An isolated polynucleotide encoding the anti-human IL-17A monoclonal antibody of claim 1.

7. The polynucleotide of claim 6, wherein the nucleotide sequence encoding the heavy chain variable region of the antibody comprises SEQ ID NO:1, and the nucleotide sequence encoding the light chain variable region of the antibody comprises SEQ ID NO:3.

8. The polynucleotide of claim 6, wherein the nucleotide sequence encoding the heavy chain variable region of the antibody comprises SEQ ID NO:17, and the nucleotide sequence encoding the light chain variable region of the antibody comprises SEQ ID NO:18.

9. The polynucleotide of claim 6, wherein the nucleotide sequence encoding the heavy chain variable region of the antibody comprises SEQ ID NO:11, and the nucleotide sequence encoding the light chain variable region of the antibody comprises SEQ ID NO:13.

10. The polynucleotide of claim 6, wherein the nucleotide sequence encoding the heavy chain variable region of the antibody comprises SEQ ID NO:19, and the nucleotide sequence encoding the light chain variable region of the antibody comprises SEQ ID NO:20.

11. An expression vector, comprising the polynucleotide of claim 6.

12. An isolated host cell, comprising the expression vector of claim 11.

13. A method of preparing an anti-human IL-17A monoclonal antibody encoded by the polynucleotide in the expression vector in the host cell of claim 12, comprising the steps of: a) culturing the host cell under suitable conditions to express the antibody; and b) isolating and purifying the expressed antibody.

\* \* \* \* \*